US00PP12787P2

(12) United States Plant Patent
Trees

(10) Patent No.: US PP12,787 P2
(45) Date of Patent: Jul. 23, 2002

(54) VERBENA PLANT NAMED 'BALAZLAVI'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/808,318

(22) Filed: Mar. 14, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named Balazlavi, characterized by its lavender flowers with "eye", mounded trailing habit, and dark green leaves.

1 Drawing Sheet

BACKGROUND OF INVENTION

The present invention comprises a new and distinct verbena plant, botanically known as *Verbena hybrida*, and hereinafter referred to by the cultivar name 'Balazlavi'.

The new cultivar was developed by the inventor through a controlled breeding program during 1998 at Arroyo Grande, Calif. The objective of the breeding program was the development of verbena cultivars with semi-trailing mounded habit, continuous flowering, excellent basal branching and small, dark green foliage.

The female (seed) parent of 'Balazlavi' was the commercially available seed verbena cultivar 'Quartz Blue' (unpatented) which exhibits an upright growth habit, dark purple flowers with white "eye" and medium green foliage. The male (pollen) parent of 'Balazlavi' was the commercially available verbena cultivar 'Temari Violet' (unpatented), which exhibits a trailing growth habit, dark lavender flowers and medium green foliage.

Asexual reproduction of the new cultivar by terminal stem cuttings in Arroyo Grande, Calif. and West Chicago, Ill. has demonstrated that the characteristics of the new cultivar as herein described are firmly fixed and retained through successive generations of such asexual propagation.

SUMMARY OF INVENTION

It was found that the cultivar of the present invention:

(a) Exhibits lavender flowers with small "eye",
(b) Forms serrate, dark green foliage
(c) Exhibits a good basal branching character and
(d) Exhibits an upright mounded and trailing growth habit.

When the new cultivar of the present invention is compared to its male parent, 'Temari Violet', it is found that the new cultivar, is shorter, has longer internodes, larger leaves, larger inflorescences and different flower and calyx color. When compared to 'Temari Patio Blue', (unpatented), 'Balazlavi' is more compact, has longer internodes, longer petioles, fewer flowers per inflorescence and different flower and calyx color as detailed in TABLE A.

When the new cultivar of the present invention is compared to 'Balazdapi' (co-pending U.S. Plant patent application Ser. No. 09/808,204), the new cultivar is distinguished from 'Balazdapi' primarily in petal coloration. When the new cultivar of the present invention is compared to 'Balwilapi' (co-pending U.S. Plant patent application Ser. No. 09/822,611), the new cultivar is distinguished from 'Balwilapi' primarily in petal coloration.

BRIEF DESCRIPTION OF PHOTOGRAPH

The accompanying photograph illustrates the overall appearance of the new cultivar as true as it is reasonably possible to obtain colored reproductions of this type. Color in the photograph may differ slightly from the color values cited in the detailed botanical description which accurately describe the actual colors of the new Verbena. The photograph comprises a side perspective view of 'Balazlavi'. The plants were grown in a greenhouse at West Chicago, Ill., U.S.A.

DETAILED BOTANICAL DESCRIPTION

The 'Balazlavi' cultivar has not been observed under all possible environmental conditions to date. Accordingly, it is possible that the phenotype may vary somewhat with variations in the environment, such as temperature, light intensity, and day length The chart used in the identification of colors described herein is the R.H.S. Colour Chart of The Royal Horticultural Society, London, England. The color values were determined on Aug. 15, 2000. The readings were taken between 1:00 and 3:00 p.m. under natural daylight conditions. The plants used for the descriptions were produced from cuttings taken from stock plants and grown for about 11 weeks after planting rooted cuttings in 10 cm pots in a double poly covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balazlavi'.

Parentage:

*Female parent.*—'Quartz Blue'.

*Male parent.*—'Temari Violet'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8 to 10 weeks after the planting of a rooted cutting, commonly measures approximately 23.5 cm in height and approximately 36.5 cm in width.

*Form.*—Upright mounded and trailing.

*Stem.*—Tetragonal, approximately 2 mm in diameter with moderate pubescence, 144A with no anthocyanin coloration. Internode length is approximately 3.1 cm.

*Foliage.*—Leaves are opposite, ovate with serrate margin, broadly acute apex, attenuate base with medium to dense short, soft pubescence on upper and lower surface, especially along veins on lower surface. Approximately 2.9 cm in length and approximately 1.6 cm at widest point. Upper surface is slightly darker than 137A, lower surface is 137B; venation of upper and lower surface is 144D. Petiole length is approximately 4 mm; color is 144D.

Flowering description:

*Flowering habit.*—Freely flowering.

*Natural flowering season.*—Year round in greenhouse environment, April through October in outdoor garden.

*Inflorescence type.*—Corymb. Approximately 2.9 cm deep and 5.4 cm in diameter with approximately 16 fully open flowers per inflorescence at any one time.

*Bud.*—Round to oval, approximately 4 mm in diameter, 84A.

*Petals.*—Five, fused at base, non overlapping, flat.

*Flower diameter.*—Approximately 1.9 cm. Corolla tube approximately 2.1 cm long.

*Calyx.*—Approximately 1.3 cm in length, 2 mm in diameter, 5 toothed, 5 ribbed, with stipules. Color is 143A (both surfaces) with no anthocyanin coloration.

*Flower color.*—Upper surface of fully opened flower is between 67A and 67B, fades to between 80A and 80B with age; Lower surface of fully opened flower is 84C. Base of all petals is 2D producing a very small 'eye'. Whiskers of 10D surround opening to corolla tube.

*Reproductive organs.*—There are 4 stamens; one pistil; pollen color is 10A.

Seed production: Seed production has not been observed.

Disease resistance: Resistance to pathogens has not been observed.

TABLE A

| CHARACTERISTIC | 'BALAZLAVI' | 'TEMARI VIOLET' | 'TEMARI PATIO BLUE' |
|---|---|---|---|
| PLANT HEIGHT | 23.5 CM | 27 CM | 30 CM |
| INTERNODE LENGTH | 3.1 CM | 2.5 CM | 1.1 CM |
| PETIOLE LENGTH | 4 MM | 3 MM | 1.5 MM |
| LEAF LENGTH X LEAF WIDTH | 2.9 CM × 1.6 CM | 2 CM × 1.4 CM | 2.2 CM × 1.5 CM |
| PEDUNCLE LENGTH | 3.4 CM | 1.7 CM | 2.8 CM |
| INFLORESCENSE DIAMETER | 5.4 CM | 4.3 CM | 4.8 CM |
| NUMBER OF FLOWERS PER INFLORESCENCE | 16 | 16 | 19 |
| FLOWER DIAMETER | 1.9 CM | 2.2 CM | 2 CM |
| CALYX COLOR | 143A WITH NO ANTHOCYANIN COLORATION | 144A WITH ANTHOCYANIN COLORATION ALONG RIBS | 144A WITH ANTHOCYANIN COLORATION AT ONE SPOT ALONG RIM |
| PETAL COLOR-UPPER SURFACE-RHS | BETWEEN 67A AND 67B WITH BASE OF 2D FORMING AN 'EYE' | BETWEEN 80A AND 81A | BETWEEN 90B AND 89C |
| PETAL COLOR-LOWER SURFACE-RHS | 84C | 84A AT MARGIN; 85B AT BASE | BETWEEN 90C AND 90D |

I claim:

1. A new and distinct cultivar of *Verbena hybrida* plant named 'Balazlavi' substantially as herein shown and described, which:

(a) Exhibits lavender flowers with small "eye", (b) Forms serrate, dark green foliage, (c) Exhibits a good basal branching character and (d) Exhibits a upright mounded and trailing growth habit.

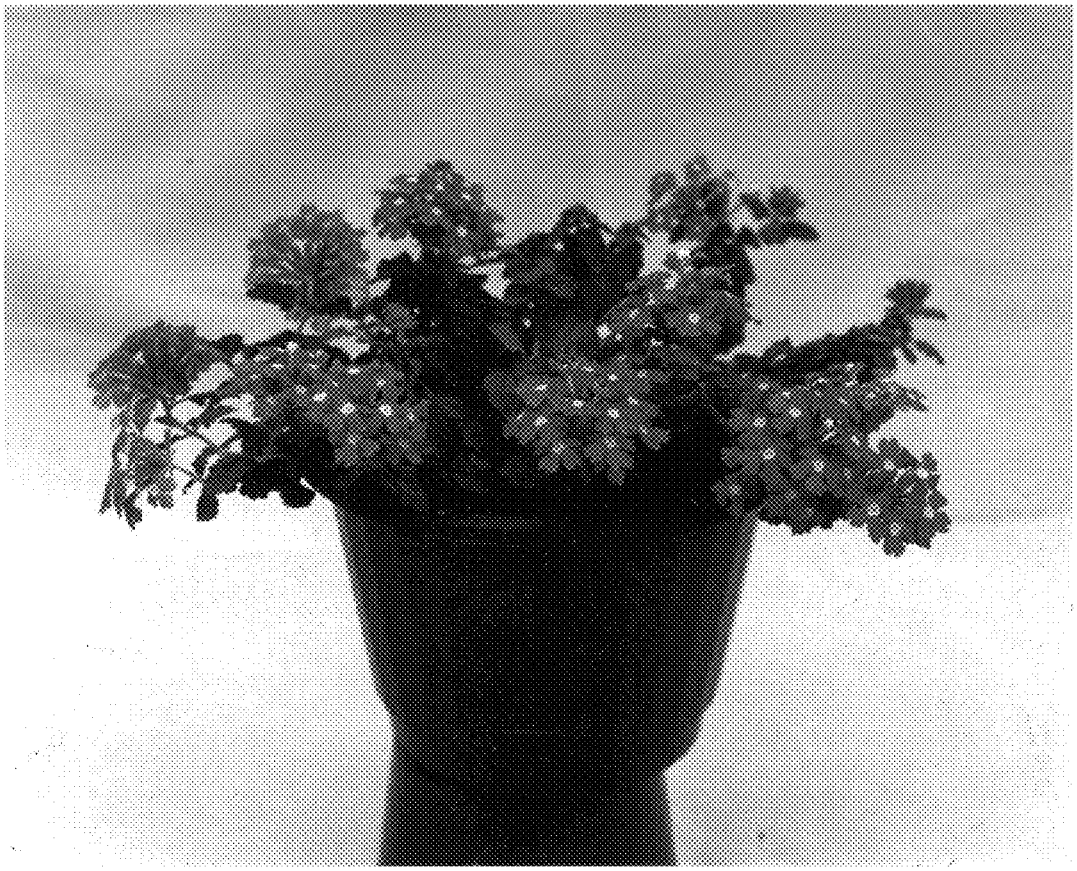

* * * * *